United States Patent [19]
Savage et al.

[11] Patent Number: 5,980,830
[45] Date of Patent: *Nov. 9, 1999

[54] PORTABLE MODULAR BLOOD ANALYZER WITH SIMPLIFIED FLUID HANDLING SEQUENCE

[75] Inventors: Douglas Robert Savage, Del Mar; Ronald Lee Lawrence, San Diego, both of Calif.

[73] Assignee: SenDx Medical, Inc., Carlsbad, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/650,341

[22] Filed: May 20, 1996

[51] Int. Cl.⁶ ..................................................... G01N 35/00
[52] U.S. Cl. ............................. 422/81; 422/63; 422/100; 422/103; 436/43; 436/180
[58] Field of Search ................................. 422/61, 58, 68, 422/81, 100, 104, 103; 436/43, 46, 52, 174, 180, 183

[56] References Cited

U.S. PATENT DOCUMENTS

| | | | |
|---|---|---|---|
| 3,874,850 | 4/1975 | Sorensen et al. | 23/230 |
| 4,003,705 | 1/1977 | Buzza et al. | 23/230 |
| 4,116,336 | 9/1978 | Sorensen et al. | 206/524.8 |
| 4,415,085 | 11/1983 | Clarke et al. | 206/526 |
| 4,649,028 | 3/1987 | Kaltenbach et al. | 422/100 |
| 4,786,394 | 11/1988 | Enzer et al. | 204/401 |
| 4,871,439 | 10/1989 | Enzer et al. | 204/401 |
| 4,888,295 | 12/1989 | Zaromb et al. | 436/161 |
| 5,004,583 | 4/1991 | Guruswamy et al. | 422/58 |
| 5,084,158 | 1/1992 | Inoue | 204/411 |
| 5,279,797 | 1/1994 | Burns et al. | 422/102 |
| 5,284,568 | 2/1994 | Pace et al. | 204/403 |
| 5,477,883 | 12/1995 | Totten | 137/614.03 |
| 5,486,335 | 1/1996 | Wilding et al. | 422/55 |
| 5,520,787 | 5/1996 | Hanagan et al. | 204/409 |
| 5,529,635 | 6/1996 | Miyake et al. | 364/497 |
| 5,547,555 | 8/1996 | Schwartz et al. | 204/418 |
| 5,555,908 | 9/1996 | Edwards et al. | 137/329.1 |
| 5,665,315 | 9/1997 | Robert et al. | 422/102 |

FOREIGN PATENT DOCUMENTS 2 100 859  1/1983  United Kingdom .

*Primary Examiner*—Long V. Le
*Attorney, Agent, or Firm*—Fish & Richardson P.C.

[57] ABSTRACT

A portable, modular blood analyzer capable of analyzing multiple blood values in an inexpensive, relatively simple, easy-to-use and easy-to-maintain instrument. The invention comprises a three-part system including an analyzer body, calibrant cartridge, and sensor cartridge. A modular calibrant cartridge is insertable into the analyzer body, and contains all necessary calibrant fluids as well as a waste container. A modular sensor cartridge having integral pump tubing plugs into the analyzer body for easy removal and replacement of the sensor elements. The analyzer body internally has modular units including an electronics module, a display module, and a fluidics/printer module. The analyzer uses a single pump head to aspirate blood only to a sensor array within the sensor cartridge. This action is accomplished by aspirating blood by rotating a peristaltic pump in one direction during a first portion of an analysis cycle, and by reversing the pump and flushing the blood from the sensor cartridge with fluid pumped from the opposite direction during a second portion of an analysis cycle. Accordingly, blood contacts only a small portion of the analyzer mechanism, most of which is disposable. Because all valves are "downstream" from the single pump, no blood products pass through any valves. The analyzer fluid handling section is easily cleaned by removal of the sensor cartridge, yielding a single tube pathway. A short path length for blood travel permits using blood samples as small as 200 μl. The analyzer is lightweight and modular in design and is fully automatic.

21 Claims, 7 Drawing Sheets

PORTABLE MODULAR BLOOD ANALYZER WITH SIMPLIFIED FLUID HANDLING SEQUENCE

RELATED APPLICATIONS

This application is related to the following co-pending U.S. patent applications, all assigned to the assignee of the present invention:

(1) Ser. No. 08/650,624, now U.S. Pat. No. 5,820,825 entitled "Waste Container for Portable Blood Analyzer";
(2) Ser. No. 08/650,340, now U.S. Pat. No. 5,885,533 entitled "Integral Fluid and Waste Container for Blood Analyzer";
(3) Ser. No. 08/650,622, now abandoned, entitled "Blood Gas/Electrolyte Calibrator and Method for Use";
(4) Ser. No. 08/650,465, entitled "Reference Solution Container for Blood Gas/Electrolyte Measuring System";
(5) Ser. No. 08/648,692, now U.S. Pat. No. 5,718,816 entitled "Locking Sensor Cartridge with Integral Fluid Port, Electrical Connections, and Pump Tube";
(6) Ser. No. 08/649,009, entitled "Sensors with Subminiature Through Holes and Method for Fabricating Such Sensors";
(7) Ser. No. 08/648,675, entitled "Electronic Wiring Substrate with Subminiature Through Holes and Method for Fabricating Such Sensors";
(8) Ser. No. 08/648,676, entitled "A Sensor Cartridge for an Analyte Analyzer";
(9) Ser. No. 08/648,694, now U.S. Pat. No. 5,844,200 entitled "Method and Apparatus for Drilling Subminiature Through Holes in a Sensor Substrate"; and
(10) Ser. No. 08/649,525, now U.S. Pat. No. 5,869,971 entitled "Method and Apparatus for Ratiometric Measurement of Hematocrit".

BACKGROUND OF THE INVENTION

1. Field of the Invention

This invention relates to blood analyzers, and more particular to portable blood analyzers capable of analyzing multiple analytes.

2. Description of Related Art

Blood analyzers are medical instruments capable of analyzing one or more analytes, such as blood values for oxygen, carbon dioxide, pH, hematocrit, and electrolytes, such as potassium, sodium, and calcium ions. Most prior art blood analyzers capable of measuring more than one analyte are complex, requiring specialized service skills and operator experience. Such multiple analyte blood analyzers have generally weighed in excess of 30 pounds, and have had sensor electrodes and plumbing (fluid path) that are complicated and require specialized knowledge to service. Many such blood analyzers require tonometered gases in rigid or semi-rigid tanks to calibrate the sensors.

Prior blood analyzers have also often suffered from problems relating to clotting or blockage by proteinaceous materials which occlude fluid handling elements of the instrument. Analyzers which carry blood samples over long distances through multiple banks of electrodes are more susceptible to such problems. Also, blood elements tend to obstruct traditional valving systems. When blood obstruction occurs in instrumentation, intensive disassembly and servicing has generally been required. Generally, blood analyzers having longer blood paths have more valves, and are generally complex and costly.

Accordingly, after noting the limitations of the above-described prior art, the inventors of the present invention have devised a new blood analyzer that overcomes these problems.

SUMMARY OF THE INVENTION

The present invention comprises a portable, modular blood analyzer capable of analyzing multiple blood values in an inexpensive, relatively simple, easy-to-use and easy-to-maintain instrument. In the preferred embodiment of the present invention, the invention comprises a three-part system including an analyzer body, calibrant cartridge, and sensor cartridge. A modular calibrant cartridge is insertable into the analyzer body, and contains all necessary calibrant fluids as well as a waste container. A modular sensor cartridge having integral pump tubing plugs into the analyzer body for easy removal and replacement of the sensor elements. The analyzer body internally has modular units comprising an electronics module, a display module, and a fluidics/printer module.

The inventive analyzer also uses a single pump head to aspirate blood only to a sensor array within the sensor cartridge, thus minimizing exposure of blood to internal valves and fluid handling circuits within the analyzer body. This action is accomplished by aspirating blood by rotating an peristaltic pump in one direction during a first portion of an analysis cycle, and by reversing the pump and flushing the blood from the sensor cartridge with fluid pumped from the opposite direction during a second portion of an analysis cycle. Accordingly, blood contacts only a small portion of the analyzer mechanism, most of which (i.e., the sensor cartridge) is disposable. Because all valves are "downstream" from the single pump, no blood products pass through any valves. The analyzer fluid handling section is easily cleaned by removal of the disposable sensor cartridge, yielding a single tube pathway. A short path length for blood travel permits using blood samples as small as about 200 µl, and preferably less than about 150 µl.

The analyzer is light-weight and modular in design and is fully automatic. The analyzer can be serviced and operated by non-skilled or lesser skilled personnel, who can insert and remove the low-cost sensor cartridge and calibrant cartridge without tools or special knowledge of the mechanism.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings indicate like elements.

DETAILED DESCRIPTION OF THE INVENTION

Throughout this description, the preferred embodiment and examples shown should be considered as exemplars, rather than as limitations on the present invention.

Figure 1:
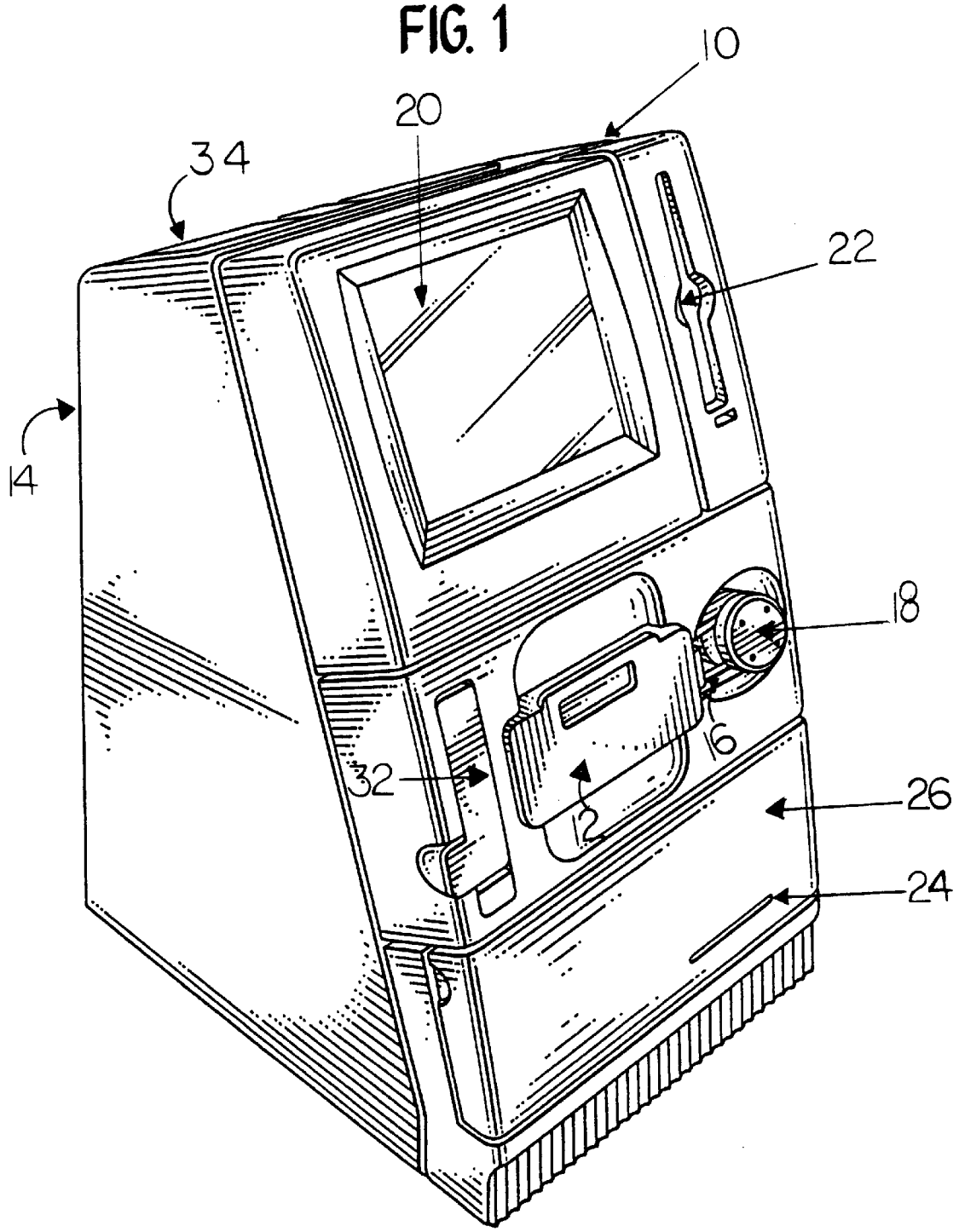
FIG. 1 is a perspective view of the preferred embodiment of the blood analyzer of the present invention.
Figure 2:
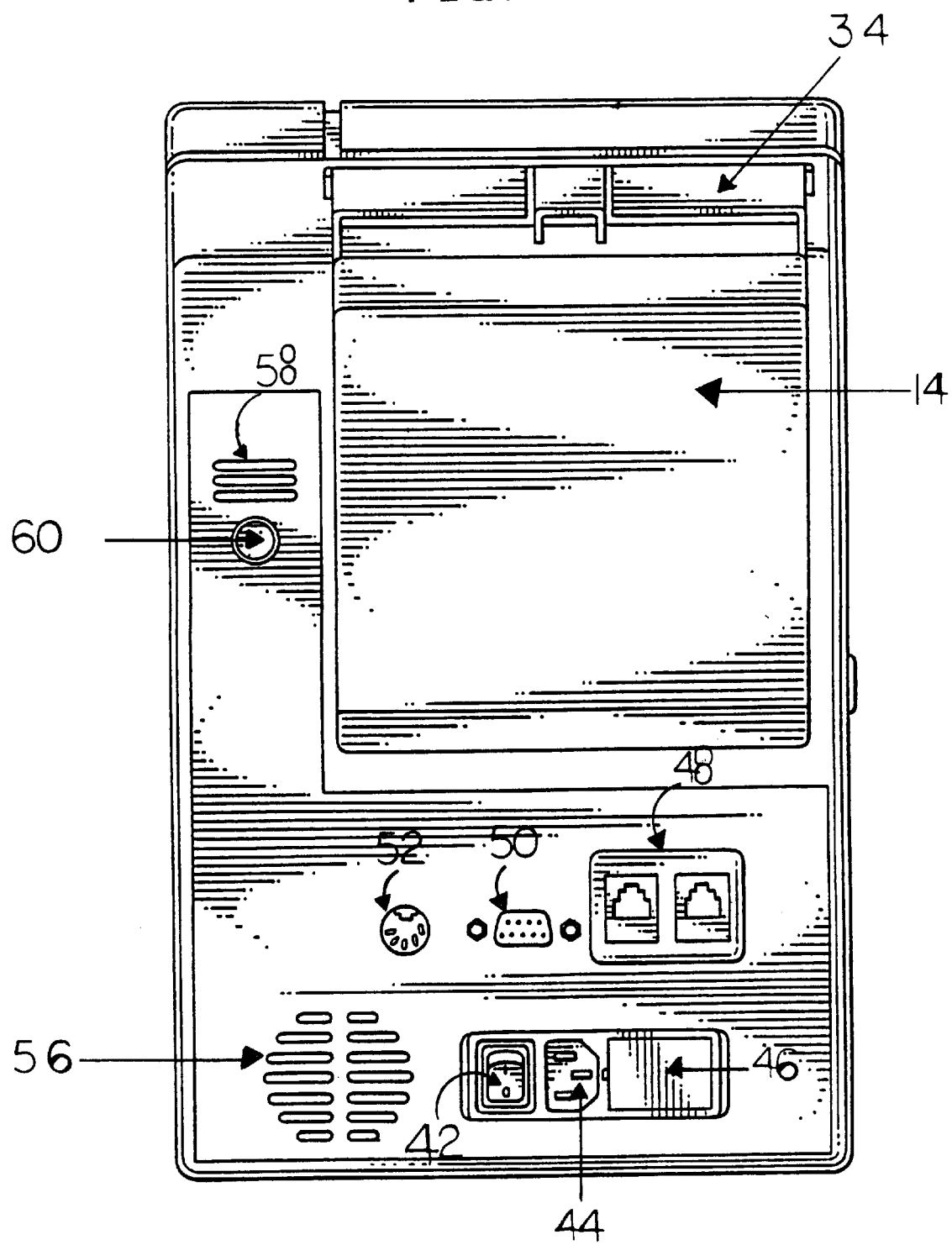
FIG. 2 is a rear plan view of the preferred embodiment of the blood analyzer of the present invention.
Figure 3:
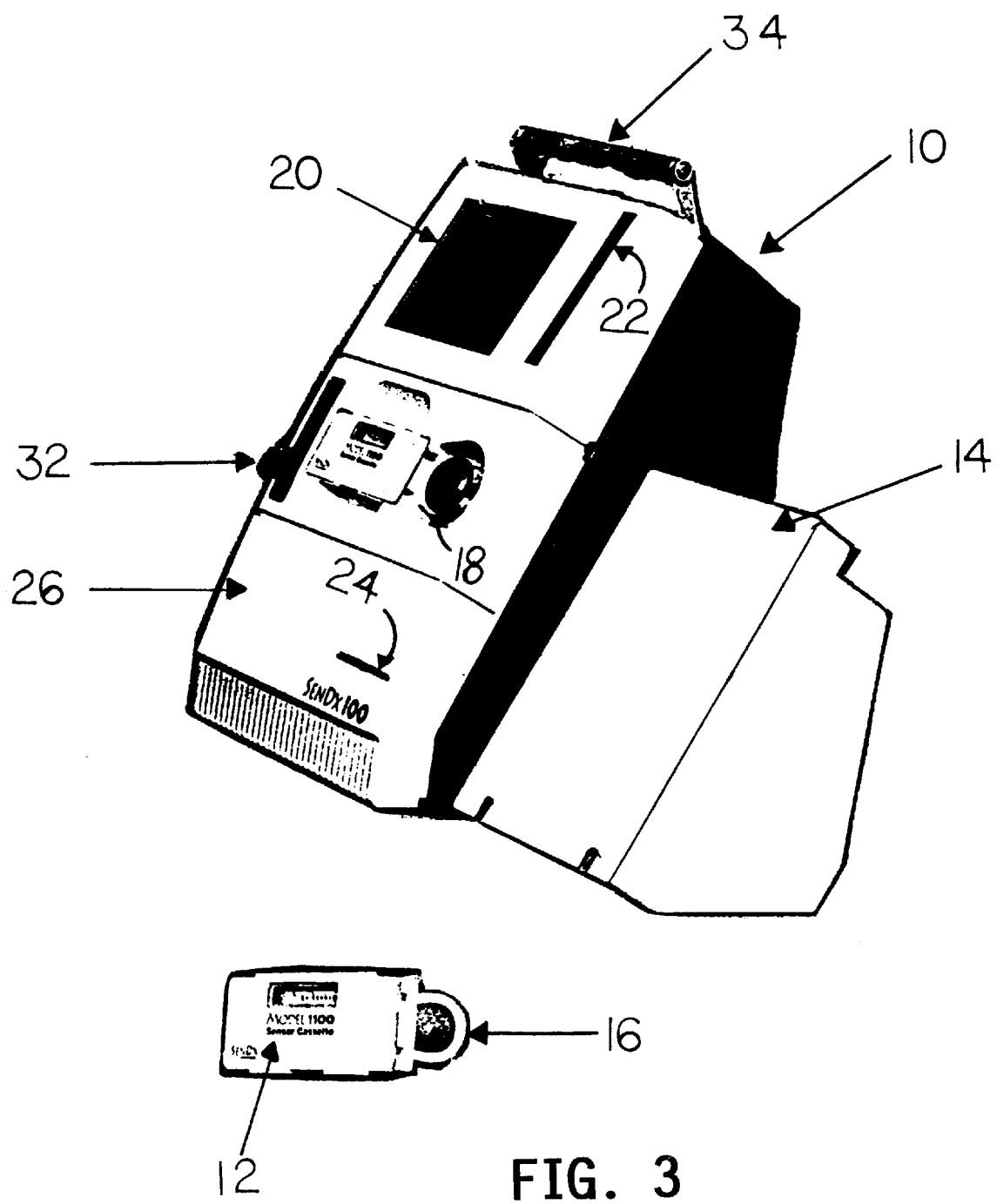
FIG. 3 is a perspective view of the preferred embodiment of the blood analyzer of the present invention with the sensor cartridge and calibrant cartridge next to the analyzer body.
Figure 4:
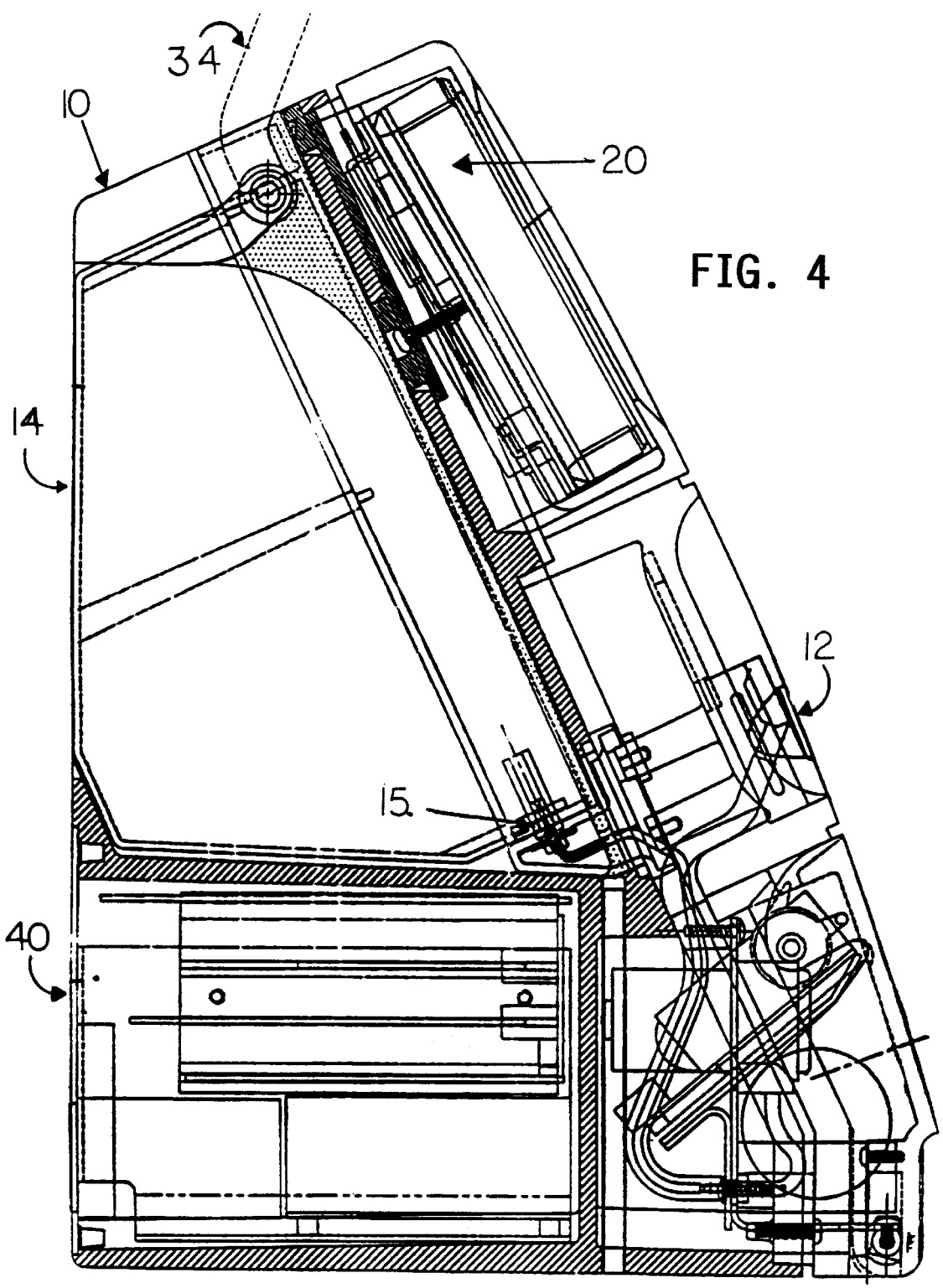
FIG. 4 is an x-ray side view of the preferred embodiment of the blood analyzer of the present invention.

FIG. 1 is a perspective view of the preferred embodiment of the blood analyzer 10 of the present invention. FIG. 2 is a rear plan view of the same analyzer 10. FIG. 3 is a perspective view of the analyzer 10 of the present invention with a sensor cartridge 12 and calibrant cartridge 14 next to the body of the analyzer 10. FIG. 4 is an x-ray side view of the blood analyzer 10.

The analyzer 10 includes a plug-in sensor cartridge 12 that provides sensors for measuring such blood characteristics as oxygen, carbon dioxide, pH, hematocrit, and electrolytes, such as potassium, sodium, and calcium ions. However, fewer or more analyte sensors can be included within the sensor cartridge 12. The sensor cartridge 12 preferable plugs in so that electrical contacts and plumbing connections are via "press-on" or "bayonet" type fittings without tools. In the preferred embodiment, a latch mechanism may be used to hold the removable sensor cartridge 12 in place. A loop of elastomeric tubing 16 attached to the sensor cartridge 12 is stretched to fit around a peristaltic pump head 18. (See also FIG. 6). The sensor cartridge 12 and elastomeric tubing 16 are preferably made of transparent materials so that the flow of blood samples and fluids can be seen at all times, permitting visual detection of bubbles that can adversely affect operation of the analyzer 10. When attached to the analyzer 10, the sensor cartridge 12 is in fluid communication with the calibrant cartridge 14 and in signal communication with analyte determination circuitry within the analyzer (note that some electronics may be included within the sensor cartridge itself). Details of the construction and operation of a preferred sensor cartridge 12 are set forth in related patent applications (5) through (10) identified above under RELATED APPLICATIONS.

The analyzer 10 includes a plug-in calibrant cartridge 14. The calibrant cartridge 14 preferably houses at least two flexible bags containing calibrant fluids (Calibrant A and Calibrant B), and an initially empty waste bag. The calibrant cartridge 14 preferable plugs in so that plumbing connections are via "press-on" or "bayonet" type fittings 15, such as a Luer fitting, without tools. As shown in FIG. 4, the fittings 15 are preferably at the bottom of the calibrant cartridge 14 to provide a gravity assist to calibrant fluid flow and to provide a very short fluid path for the overall system. In the preferred embodiment, a latch mechanism 15 (shown in FIG. 2) in each removable calibrant cartridge 14 is used to positively engage the body of the analyzer 10, to ensure a gas-tight fit of all fluid connections (necessary to maintain proper calibrant gas ratios) and to prevent inadvertent detachment of the calibrant cartridge 14. When both the calibrant cartridge 14 and the sensor cartridge 12 are installed within the analyzer 10, the sensor cartridge 12 is in fluid communication with each calibrant fluid container and the waste container in the calibrant cartridge 14 via internal plumbing within the analyzer 10. Details of the construction and operation of a preferred calibrant cartridge 14 are set forth in related patent applications (1) and (2) identified above under RELATED APPLICATIONS.

The preferred embodiment of the analyzer 10 includes a touch-screen display panel 20 for displaying instructions, indicating test results and messages, and providing an input means for entering in data about calibrants, patients, accounting information, etc. The user interface for the display panel 20 is preferably menu or icon driven, thereby substantially reducing the amount of keyboard input required by a user. In the preferred embodiment, a removable media data storage device 22, such as a floppy disk drive, is provided to allow capturing of data generated by the analyzer 10 and to provide a convenient means of reprogramming the internal electronics of the analyzer 10.

The preferred embodiment of the analyzer 10 includes a fluidics/printer module 24 that comprises the a fluidics module board 122 (shown in FIG. 5), internal plumbing, valves, manifolds, etc. for routing fluids to and from the sensor cartridge 12 and calibrant cartridge 14, as well as a printer 25 (shown in FIG. 5) hidden behind a face panel 26 that can be used to print out varied information, such as the results of a particular blood analysis. The printer may be, for example, a thermal dot matrix printer. Use of the printer is optional, since results of an analysis may be communicated by means of the display panel 20 or transmitted to another site. If necessary, the fluidics/printer module 24 can be removed and replaced as a unit. By locating the fluidics hardware and printer within a module, the time required to service the analyzer is substantially reduced.

A sample port stylus 30 (shown in FIG. 6) is hidden behind a flip-up panel 32 to protect it from contamination and damage when not in use. A convenient carrying handle 34 is provided to lift the analyzer 10, which, in the preferred embodiment, weighs less than about 20 lbs. with a filled calibrant cartridge 14 and the sensor cartridge 12 in place. The analyzer 10 preferably has dimensions no greater than about 12"W×12"D×12"H for convenient handling and siting, such as at a nursing station or other point-of-care placement.

Referring to FIG. 4, the rear bottom portion of the analyzer 10 includes a power supply and electronics bay 40 for housing a computer board. In the preferred embodiment, a battery backup unit is provided within the power supply and electronics bay 40 to provide power for a significant time (e.g., one hour) to the analyzer 10 in the event of a power failure. This feature is particularly important in a medical setting.

Referring to FIG. 2, the back panel of the analyzer 10 preferably includes a power switch 42, power connector 44, fuse box 46, modem line-in and line-out connector 48, input/output port (e.g., an RS-232 serial port) 50, an auxiliary keyboard connecter 52, fan vent port 56, speaker grill 58, and display contrast adjustment 60. Other ports may be provided as desired, such as a parallel printer port, a local area network connector, barcode reader port, etc.

Figure 5:
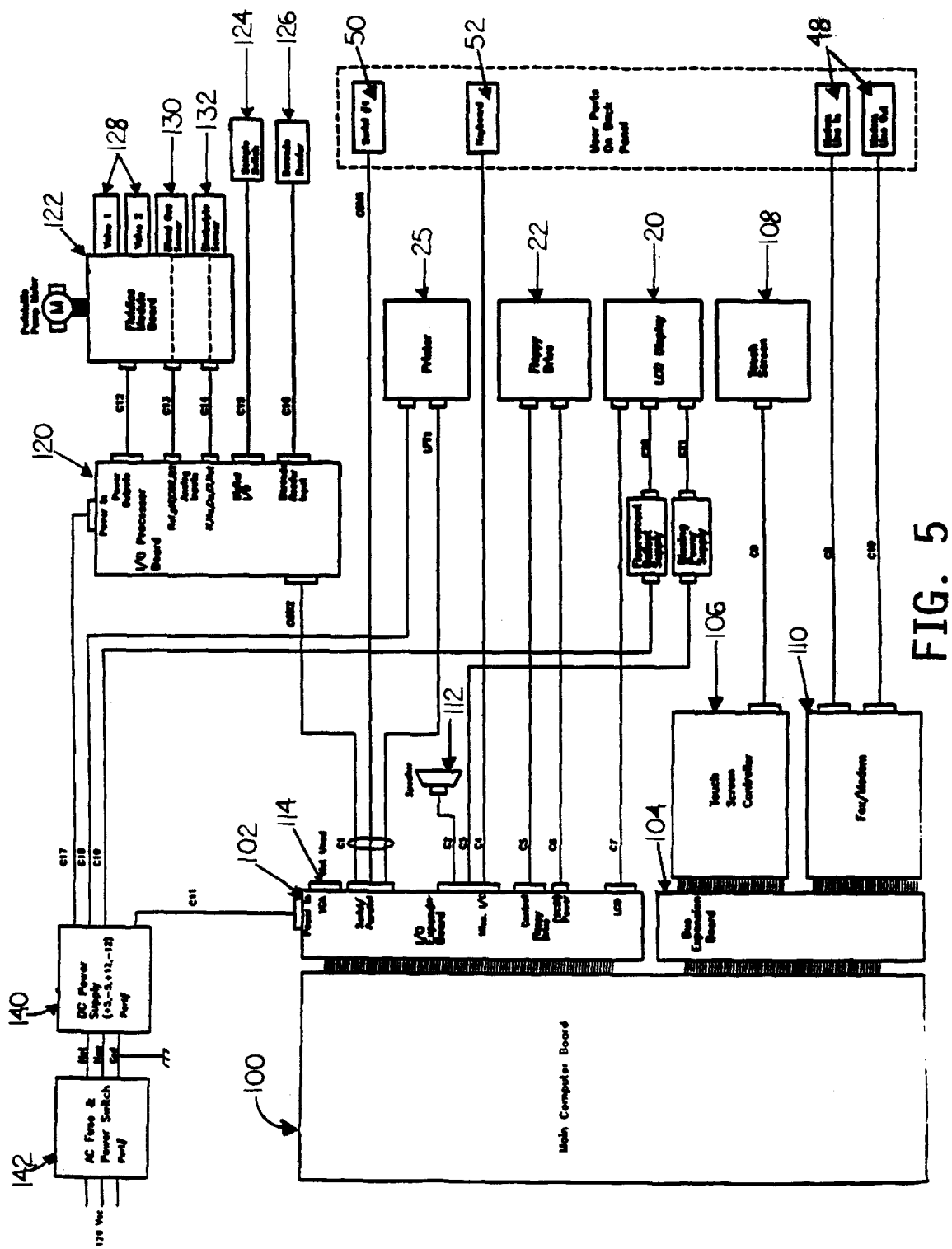
FIG. 5 is a schematic of the electrical and electronic connections of the preferred embodiment of the blood analyzer of the present invention.

FIG. 5 is a schematic of the electrical and electronic connections of the preferred embodiment of the blood analyzer 10 of the present invention. A main computer board 100 is coupled to an input/output expander board 102 and a bus expansion board 104. In the preferred embodiment, the bus expansion board 104 is coupled to a touch screen controller 106 which is in turn coupled to the touch screen 108. An optional fax/modem board 110 is provided for remote communication with the analyzer 10, which permits a variety of functions, such as remote diagnostics and per use billing. In the preferred embodiment, input/output expander board 102 is coupled in known fashion to a speaker 112, the display panel 20, the floppy drive 22, a printer 25, and the input/output port 50 and auxiliary keyboard connecter 52 on the back panel of the analyzer 10. A video port (e.g., a VGA standard port) 114 may be provided if desired for an auxiliary display.

Also coupled to the main computer board 100 is an input/output processor board 120, which is coupled to a fluidics module board 122, a sample switch 124, and a barcode reader 126. By monitoring the sample switch 124, the input/output processor board 120 detects when the sample port stylus 30 is positioned to receive a sample. The barcode reader 126 is used to enter barcoded data on new calibrant cartridges 14 and/or sensor cartridges 12.

The fluidics module 122 controls at least one valve 128 under command of the main computer board 100 via the input/output processor board 120, and receives and conditions signals from one or more blood gas sensors 130 and/or one or more electrolyte sensors 132. Received signals from the fluidics module 122 are transmitted to the input/output processor board 120 and processed in the main computer board 100.

Power to all systems is provided in conventional fashion by a DC power supply 140 coupled to an AC fuse and power switch 142.

Figure 6:
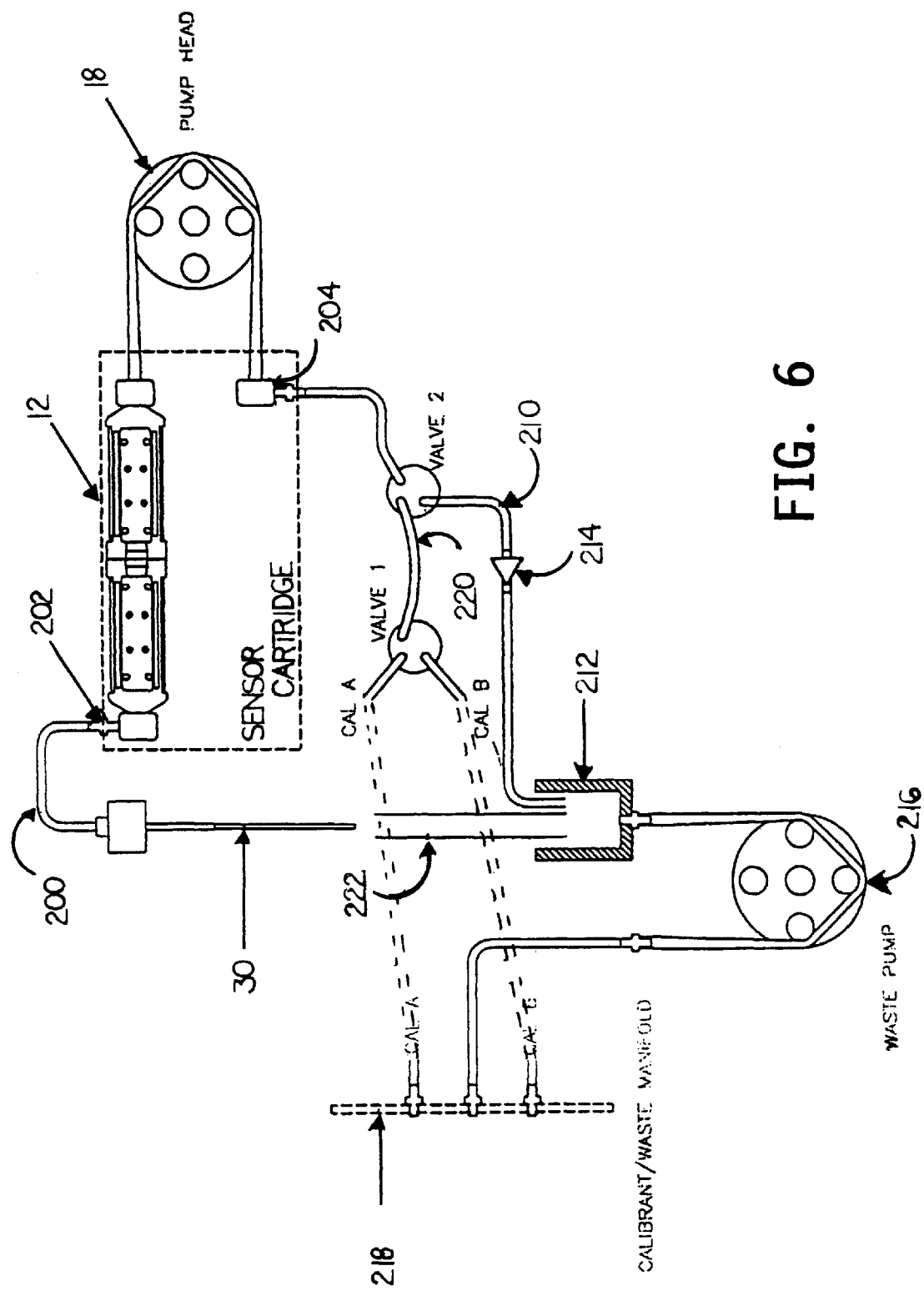
FIG. 6 is a block diagram of the fluid flow path of the preferred embodiment of the blood analyzer of the present invention.

FIG. 6 is a block diagram of the fluid flow path of the preferred embodiment of the blood analyzer of the present invention. The sample port stylus 30 is coupled via a short (preferably less than about 7 cm) inlet tube 200 (internal to the analyzer 10) to a first port 202 the sensor cartridge 12. The elastomeric tubing loop 16 attached to the sensor cartridge 12 is stretched as shown around the peristaltic pump head 18. In the preferred embodiment, the pump head 18 provides bidirectional rotary motion that moves fluid through the tubing loop 16 in known fashion. However, other types of peristaltic pump motion may be used, so long as it is bidirectional (alternatively, two pump heads may be used, each unidirectional but pumping in different directions). Further, the pump head may be configured so that the tubing loop 16 need not be wrapped around the pump head 18 by having, for example, pinch rollers that engage the tubing loop 16 along the plane formed by the tubing loop 16 (from either the front or the back).

The sensor cartridge 12 is attached through a second port 204 to bidirectional Valve 2, which is preferably an electrically actuated two-way valve. A first port of Valve 2 is coupled to a waste path 210 to a waste collector 212. Optionally, a backflow prevention valve 214 is provided to keep waste fluid from re-contacting Valve 2. The output of the waste collector 212 may be directly coupled to a waste container using gravity flow. However, in the preferred embodiment, to keep all fluids contained and away from human contact, and to provide ease of use, a peristaltic waste pump head 216 is provided to actively pump waste fluid to a waste bag within the removable calibrant cartridge 14. In the preferred embodiment, the calibrant cartridge 14 plugs into the analyzer 10 via a calibrant/waste manifold 218.

A second port of Valve 2 is coupled to bidirectional Valve 1 via a calibrant path 220. A first port of Valve 1 is coupled via tubing to Calibrant A within an attached calibrant cartridge 14. A second port of Valve 1 is coupled via tubing to Calibrant B within an attached calibrant cartridge 14.

When properly operated, three fluid paths are formed due to the settings of Valve 1 and Valve 2, and the direction of pumping by the pump head 18:

(1) from the sample port stylus 30 through the sensor cartridge 12 through Valve 2 to the waste path 210 and on to the waste collector 212;

(2) from Calibrant A through Valve 1 through the calibrant path 220 through Valve 2 through the sensor cartridge 12 to the sample port stylus 30;

(3) from Calibrant B through Valve 1 through the calibrant path 220 through Valve 2 through the sensor cartridge 12 to the sample port stylus 30.

Figures 7, 8:
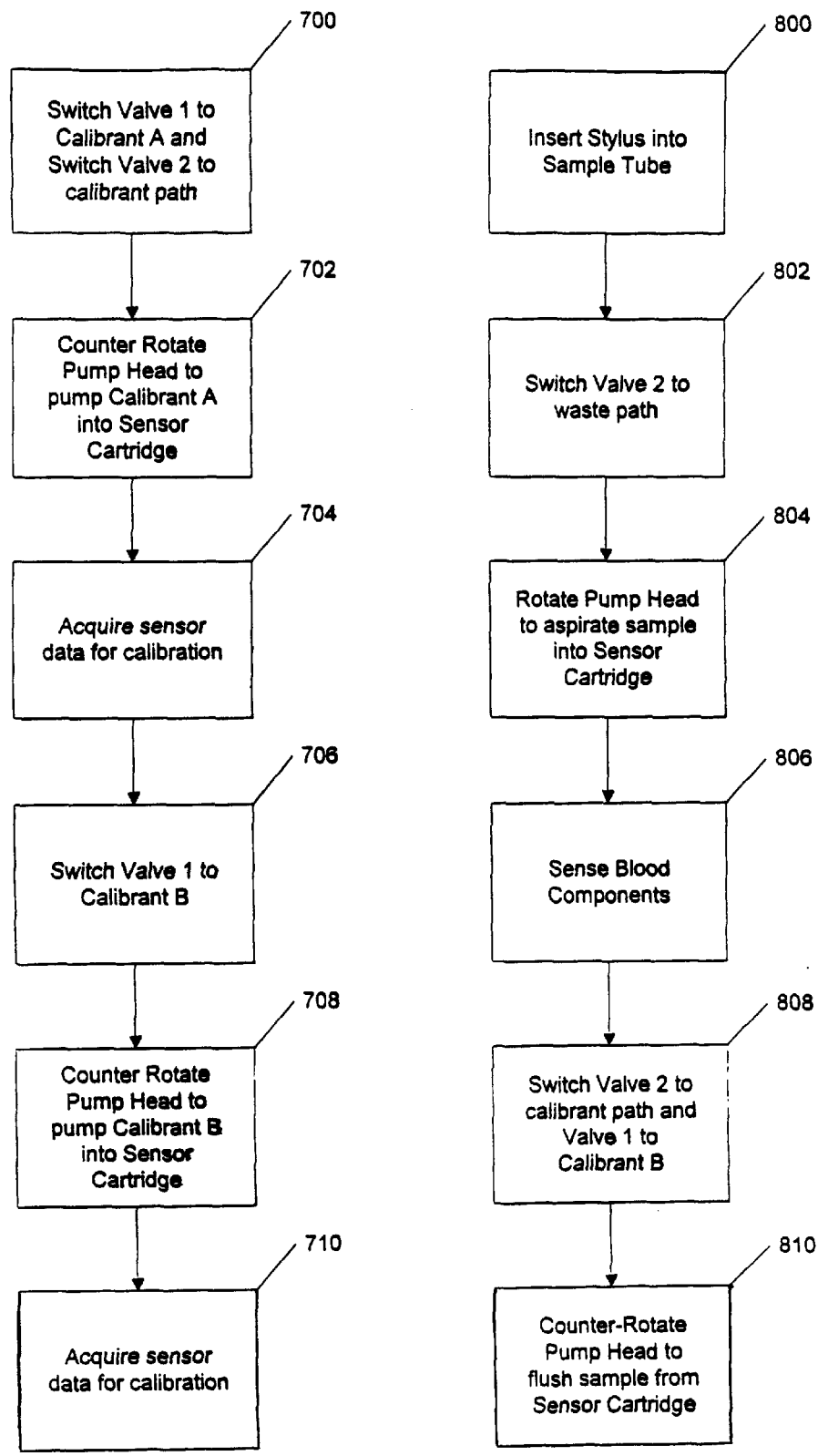
FIG. 7 is a flowchart of the fluid flow operation during calibration for the preferred embodiment of the blood analyzer of the present invention.
FIG. 8 is a flowchart of the fluid flow operation during sampling for the preferred embodiment of the blood analyzer of the present invention.

FIG. 7 is a flowchart of the fluid flow operation during calibration for the preferred embodiment of the blood analyzer of the present invention. Under control of the main computer board 100, input/output processor board 120, and fluidics module board 122, Valve 1 is switched to Calibrant A and Valve 2 is switched to the calibrant path 220 (STEP 700). In the illustrated embodiment, the pump head 18 is rotated counterclockwise so as to draw Calibrant A fluid from the calibrant cartridge 14 and pump that fluid through the sensor cartridge 12 (STEP 702). The first point of a two-point calibration of the sensors within the sensor cartridge 12 is then conducted, in known fashion (STEP 704). After the first point of calibration is done, Valve 1 is switched to Calibrant B (STEP 706). The pump head 18 is rotated counter-clockwise so as to draw Calibrant B fluid from the calibrant cartridge 14 and pump that fluid through the sensor cartridge 12 (STEP 708). The second point of a two-point calibration of the sensors within the sensor cartridge 12 is then conducted, in known fashion (STEP 710). A single-point calibration may be conducted in similar fashion, using only one of the calibrant fluids.

In all cases, the calibrant fluid exits the sensor cartridge 12 via the first port 202 of the sensor cartridge 12, and flows through the sample port stylus 30 to drain to the waste collector 212. A drain tube 222 may be provided to prevent splashing. As noted above, the optional waste pump 216 may be used to pump the waste calibrant into a waste bag within the calibrant cartridge 14.

FIG. 8 is a flowchart of the fluid flow operation during sampling for the preferred embodiment of the blood analyzer of the present invention. The sample port stylus 30 is inserted into a container of sample fluid (e.g., blood in a vial) (STEP 800). Under control of the main computer board 100, input/output processor board 120, and fluidics module board 122, Valve 2 is switched to the waste path 210 (STEP 802). In the illustrated embodiment, the pump head 18 is rotated clockwise so as to draw a sample through the sample port stylus 30 and into the sensor cartridge 12 (STEP 804). The desired sample components may then be sensed within the sensor cartridge 12 (STEP 806). Any calibration fluid that had been in the sensor cartridge 12 (e.g., from prior flushing or calibration) exits the sensor cartridge 12 via second port 204 and passes through Valve 2 to the waste path 210.

After a sample has been analyzed, Valve 2 is switched to the calibrant path 220 and Valve 1 is switched to a flushing calibrant (Calibrant B in this example) (STEP 808). The pump head 18 is rotated counter-clockwise so as to draw Calibrant B fluid from the calibrant cartridge 14 and pump that fluid through the sensor cartridge 12, thereby flushing the sample out of the sensor cartridge 12. The waste fluid (sample and Calibrant B) exits the sensor cartridge 12 via the first port 202 of the sensor cartridge 12, and flows through the sample port stylus 30 to drain to the waste collector 212.

Importantly, the control system ensures that the whole undiluted blood sample is never pumped past the pump head 18, and thus is never in contact with either Valve 2 or Valve 1.

In an alternative embodiment, Valve 1 can be eliminated by changing Valve 2 from a three-way valve as shown, to a four-way valve, and directly coupling Calibrant A and Calibrant B to Valve 1. Any other valving system that provides the three paths described above can also be used, such as by using three two-way valves.

As a result of this simple fluidics system, the invention minimizes exposure of internal valves and fluid handling circuits within the analyzer body to samples. Accordingly, blood contacts only a small portion of the analyzer mechanism, most of which (i.e., the sensor cartridge) is disposable. Because all valves are "downstream" from the single pump, no blood products pass through any valves. Only a single pump is required, thus reducing the cost of manufacture. The analyzer fluid handling section is easily cleaned by removal of the disposable sensor cartridge, yielding a single tube pathway. The short path length for blood through the sample port stylus 30 and inlet tube 200 permits using blood samples as small as about 200 µl, and preferably less than about 150 µl.

The control for the fluidics system is preferably accomplished via one or more control programs operating on the main computer board 100 and controlling the fluidics module board 122 through the input/output processor board 120. Program code is applied to input data to perform the functions described above and generate output information. The output information is applied to one or more output devices or actuators, as described above.

Each program is preferably implemented in a high level procedural or object oriented programming language to communicate with the computer system. However, the programs can be implemented in assembly or machine language, if desired. In any case, the language may be a compiled or interpreted language.

Each such computer program is preferably stored on a storage media or device (e.g., "flash" RAM, ROM, or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

What is claimed is:

1. A portable, modular blood analyzer capable of analyzing at least one analyte value of a blood sample, comprising:
   (a) an analyzer body including analyte determination circuitry;
   (b) a removable calibrant cartridge having at least one calibrant fluid container having calibrant fluid for performing at least one analysis of at least one analyte value of a blood sample, and having at least one waste container, the removable calibrant cartridge being configured to attach to the analyzer body without tools;
   (c) a removable sensor cartridge having integral pump tubing, the sensor cartridge including at least one sensor for performing at least one analysis of at least one analyte value of a blood sample, the removable sensor cartridge being configured to attach to the analyzer body without tools, and, when so attached, to be in fluid communication with each calibrant fluid container and the waste container and in signal communication with the analyte determination circuitry;
   (d) at least one valve situated to alternatively couple the sensor cartridge to a waste port and to at least one calibrant fluid container within the calibrant cartridge;
   (e) a sample port, in fluid communication with the sensor cartridge, for drawing a blood sample into the sensor cartridge;
   (f) a bidirectional pumping mechanism having a pump head and positioned between the sensor cartridge and each valve, for engaging the pump tubing of the sensor cartridge, and for selectively pumping in a direction towards the waste port and in a direction towards the sample port; and
   (g) the blood analyzer is for automatically:
      (1) switching each valve to couple the sensor cartridge to the waste port,
      (2) actuating the bidirectional pumping mechanism to pump in a direction towards the waste port,
      (3) drawing a blood sample into the sensor cartridge through the sample port,
      (4) sensing desired analyte values of the blood sample within the sensor cartridge,
      (5) switching each valve to couple the sensor cartridge to one of the calibrant fluid containers within the calibrant cartridge, and
      (6) reversing each pump to pump fluid from the calibrant fluid container in a direction towards the sample port, thereby flushing the blood sample from the sensor cartridge and sample port.

2. The blood analyzer of claim 1, further including, internal to the analyzer body, an electronics module embodying control circuitry for receiving input signals from the removable sensor cartridge, for generating at least one analysis of at least one analyte value of a blood sample, for outputting the results of each such analysis, and for controlling the operation of the blood analyzer.

3. The blood analyzer of claim 1, further including a display module attached to the analyzer body, for displaying results of each such analysis.

4. The blood analyzer of claim 1, further including a printer module internal to the analyzer body, for printing results of each such analysis.

5. The blood analyzer of claim 1, wherein the blood analyzer with attached removable calibrant cartridge and removable sensor cartridge, weighs less than about 20 pounds.

6. The blood analyzer of claim 1, wherein the blood analyzer with attached removable calibrant cartridge and removable sensor cartridge, measures less than about 12"W×12"D×12"H.

7. The blood analyzer of claim 1, wherein the calibrant cartridge includes a latching mechanism to maintain a gas-tight fit with the analyzer body when the calibrant cartridge is attached to the analyzer body.

8. A portable, modular blood analyzer capable of analyzing at least one analyte value of a blood sample, comprising:
   a. an analyzer body including at least one accessible pump head and analyte determination circuitry;
   b. a removable calibrant cartridge having at least one calibrant fluid container having calibrant fluid for performing at least one analysis of at least one analyte value of a blood sample, and having at least one waste container, the removable calibrant cartridge being configured to attach to the analyzer body without tools and having a bayonet fitting corresponding to each calibrant fluid container and each waste container, each calibrant fluid container bayonet fitting being directly coupled to the corresponding calibrant fluid container without flexible tubing between the calibrant container bayonet fitting and the calibrant container and being mateable to a corresponding bayonet fitting on the analyzer body to ensure a substantially gas-tight coupling between the calibrant fluid container and the analyzer body, each waste container bayonet fitting being mateable to a corresponding bayonet fitting on the analyzer body; and c. a removable sensor cartridge having integral pump tubing for peristaltic engagement with the pump head, the sensor cartridge including at least one sensor for performing at least one analysis of at least one analyte value of a blood sample, the removable sensor cartridge being configured to attach to the analyzer body without tools, and, when so attached, to be in fluid communication with each calibrant fluid container and the waste container and in signal communication with the analyte determination circuitry.

9. A portable, modular blood analyzer capable of analyzing at least one analyte value of a blood sample, comprising:

a. an analyzer body including at least one accessible pump head and analyte determination circuitry;

b. a modular removable calibrant cartridge having at least one calibrant fluid container having calibrant fluid for performing at least one analysis of at least one analyte value of a blood sample, and having at least one waste container, the removable calibrant cartridge being configured to attach to, and be removed from, the analyzer body without tools; and c. a modular removable sensor cartridge having integral pump tubing for peristaltic engagement with the pump head, the sensor cartridge including at least one sensor for performing at least one analysis of at least one analyte value of a blood sample, the removable sensor cartridge being configured to attach to, and be removed from, the analyzer body without tools, and, when so attached, to be in fluid communication with each calibrant fluid container and the waste container and in signal communication with the analyte determination circuitry.

10. The blood analyzer of claim 9, further including, internal to the analyzer body, an electronics module embodying control circuitry for receiving input signals from the removable sensor cartridge, for generating at least one analysis of at least one analyte value of a blood sample, for outputting the results of each such analysis, and for controlling the operation of the blood analyzer.

11. The blood analyzer of claim 9, further including a display module attached to the analyzer body, for displaying results of each such analysis.

12. The blood analyzer of claim 9, further including a printer module internal to the analyzer body, for printing results of each such analysis.

13. The blood analyzer of claim 9, wherein the blood analyzer with attached removable calibrant cartridge and removable sensor cartridge, weighs less than about 20 pounds.

14. The blood analyzer of claim 9, wherein the blood analyzer with attached removable calibrant cartridge and removable sensor cartridge, measures less than about 12"W×12"D×12"H.

15. The blood analyzer of claim 9, wherein the calibrant cartridge includes a latching mechanism to maintain a gas-tight-fit with the analyzer body when the analyzer body is attached to the analyzer body.

16. The blood analyzer of claim 9, wherein the sensor cartridge is insertable into a front of the analyzer with the pump head accessible from the front of the analyzer.

17. The blood analyzer of claim 9, wherein the integral pump tubing of the sensor cartridge has two ends and is mounted to the cartridge at both ends.

18. The blood analyzer of claim 17, wherein the integral pump tubing is stretched around the pump head in peristaltic engagement.

19. The blood analyzer of claim 9, wherein the integral pump tubing is visible to an operator of the analyzer while in peristaltic engagement with the pump head.

20. The blood analyzer of claim 11, wherein the integral pump tubing and display module are simultaneously viewable by an operator when the tubing is in peristaltic engagement with the pump head.

21. The blood analyzer of claim 20, wherein the integral pump tubing of the sensor cartridge has two ends and is mounted to the cartridge at both said ends.

* * * * *